United States Patent

Asada et al.

[11] Patent Number: 5,994,542
[45] Date of Patent: *Nov. 30, 1999

[54] PROCESS FOR PRODUCING 1-SUBSTITUTED TETRAHYDROQUINAZOLINES

[75] Inventors: Sachiko Asada, Takatsuki; Masashi Komatsu, Toyonaka; Shinji Nishii, Ibaraki, all of Japan

[73] Assignee: Sumitomo Chemical Company, Limited, Osaka, Japan

[*] Notice: This patent is subject to a terminal disclaimer.

[21] Appl. No.: 09/075,816

[22] Filed: May 12, 1998

Related U.S. Application Data

[63] Continuation-in-part of application No. 08/747,822, Nov. 13, 1996, Pat. No. 5,756,738.

[30] Foreign Application Priority Data

Nov. 14, 1995 [JP] Japan ................................. 7-295435
May 13, 1997 [JP] Japan ................................. 9-122242

[51] Int. Cl.$^6$ ............... C07D 239/72; C07D 401/00; C07D 413/00; C07D 419/00
[52] U.S. Cl. ............................. 544/283; 544/284
[58] Field of Search ...................... 544/283, 284

[56] References Cited

U.S. PATENT DOCUMENTS 5,304,560  4/1994  Shimazaki et al. ................. 514/259

FOREIGN PATENT DOCUMENTS 0456835A  11/1991  European Pat. Off. .
0775697   5/1997   European Pat. Off. .
232 269   1/1986   German Dem. Rep. .
01025767  3/1989   Japan .
1-25767   5/1989   Japan .

OTHER PUBLICATIONS

Goto et al., Chem. Express (1993), 8(9), 761–4 1993.
Patent Abstracts of Japan, vol. 13, No. 205 (C–595), May 15, 1989 & JP 01 025767 A (Fujisawa Pharmaceutical Co., LTD.), Jan. 27, 1989.
Süsse M. & Johne S., Monatshefte Für Chemie/Chemical Monthly, vol. 118, No. 1, 1987, pp. 71–79, XP000650958.
Billon F. et al., "Aldose reductase inhibition by 2,4–oxo and thioxo derivatives of 1,2,3,4–tetra–hydroquinazoline" European Journal of Med. Chem., vol. 25, No. 2, 1990, pp. 121–126, XP000650960.
Patent Abstracts of Japan, vol. 16, No. 13 (C–901), Jan. 14, 1992 & JP 03 232885 A (Fujisawa Pharmaceutical Co., Ltd.), Oct. 16, 1991.
El–Barbary A.A. et al., Liebigs Annalen Der Chemie, vol. 7, 1995, pp. 1371–1375, XP 000651048, "Synthesis and antiviral evaluation of quinazoline, thieno–[2,3–d]pyrimidine, and lumazine analogues of 3'–fluoro–3'–deoxythymidine (FLT)".
Patent Abstracts of Japan Publication No. 01025767, Jan. 27, 1989.

*Primary Examiner*—Mukund J. Shah
*Assistant Examiner*—Bruck Kifle
*Attorney, Agent, or Firm*—Sughrue, Mion, Zinn Macpeak & Seas, PLLC

[57] ABSTRACT

A process for producing 1-substituted tetrahydroquinazolines represented by the formula (III):

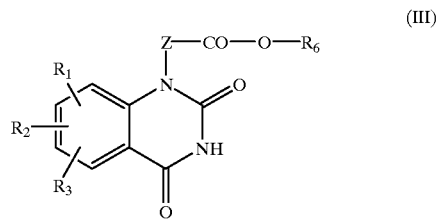

wherein Z represents a methylene group which is optionally substituted by an alkyl group; $R_6$ represents an alkyl group or an aralkyl group; $R_1$ and $R_2$ independently represent a hydrogen atom, a halogen atom, a nitro group, an azido group, an alkyl group, an alkenyl group, an aralkyl group, an alkoxy group, an alkoxycarbonyl group, an acyloxy group, or an amino group represented by $XNR_4R_5$ in which X represents a direct bond, an alkylene group or a carbonyl group, and N, $R_4$ and $R_5$ may form together a five- or six-membered heterocyclic ring or $R_4$ and $R_5$ independently represent an alkyl group or an acyloxy alkyl group; and $R_3$ represents a hydrogen atom, a halogen atom, a nitro group, an azido group, an alkyl group, an alkenyl group, an aralkyl group, an alkoxy group, or an alkoxycarbonyl group which comprises reacting tetrahydroquinazolines represented by the formula (I):

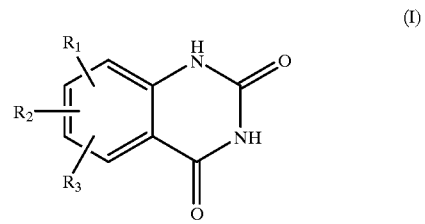

wherein $R_1$, $R_2$ and $R_3$ are as defined above with hexamethyldisilazane; and reacting the resultant product with a chloroalkanoate represented by the formula (II):

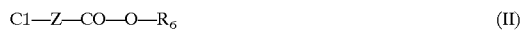

wherein Z and $R_6$ are as defined above in the presence of an iodide of an alkaline metal, followed by desilylation.

17 Claims, No Drawings

PROCESS FOR PRODUCING 1-SUBSTITUTED TETRAHYDROQUINAZOLINES

This is a Continuation-in-Part of application Ser. No. 08/747,822, filed Nov. 13, 1996 and issued as U.S. Pat. No. 5,756,738.

BACKGROUND OF THE INVENTION

1. Field of the Invention

The present invention relates to a process for producing 1-substituted tetrahydroquinazolines. More particularly, it relates to a process for producing 1-substituted tetrahydroquinazolines of formula (III) which comprises reacting tetrahydroquinazolines of formula (I) with hexamethyldisilazane; reacting the resultant product with a chloroalkanoate of formula (II) in the presence of an iodide of an alkaline metal; followed by desilylation.

2. Description of the Related Art

1-Substituted tetrahydroquinazoline of formula (III) are compounds known as intermediates for antiphlocgistics, and remedies for diabetic complications; it is also known that 1-substituted tetrahydroquinazolines of formula (III) are produced by reacting tetrahydroquinazolines of formula(I) with hexamethyldisilazane; reacting the resultant product with a bromoalkanoate; followed by desilylation (see, e.g., JP-A-64-25767).

However, this process is disadvantageous because expensive bromoalkanoate is used.

On the other hand, a process for producing 1-substituted tetrahydroquinazolines of formula (III) in which an inexpensive chloroalkanoate of formula (II) is used in place of the bromoalkanoate is also disadvantageous in that the yield is drastically lowered.

The present inventors have intensively studied the process for producing 1-substituted tetrahydroquinazolines of formula (III) so as to solve the above-mentioned drawbacks. As a result, it has been found, according to the present invention, that the desired product can be produced with high yield in an industrially advantageous manner, when the chloroalkanoate of formula (II) is used in place of the bromoalkanoate and the reaction is conducted in the presence of an iodide of an alkaline metal.

SUMMARY OF THE INVENTION

Accordingly, the present invention provides a process for producing 1-substituted tetrahydroquinazolines represented by the following formula (III):

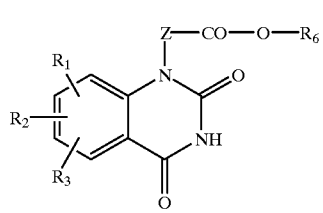

(III)

wherein

Z represents a methylene group which is optionally substituted by an alkyl group;

$R_6$ represents an alkyl group or an aralkyl group;

$R_1$ and $R_2$ independently represent a hydrogen atom, a halogen atom, a nitro group, an azido group, an alkyl group which is optionally substituted with one or more halogen atoms, an alkenyl group which is optionally substituted with one or more halogen atoms, an aralkyl group which is optionally substituted with one or more halogen atoms, an alkoxy group which is optionally substituted with one or more halogen atoms, an alkoxycarbonyl group which is optionally substituted with one or more halogen atoms, an acyloxy group, or an amino group represented by $XNR_4R_5$ in which X represents a direct bond, an alkylene group or a carbonyl group, or N, $R_4$ and $R_5$ may form together a five- or six-membered heterocyclic ring which optionally contains another hetero atom which may be substituted or when X is a direct bond or an alkylene group, $R_4$ and $R_5$ independently represent an alkyl group or when X is a carbonyl group, $R_4$ and $R_5$ independently represent an acyloxy alkyl group; and $R_3$ represents a hydrogen atom, a halogen atom, a nitro group, an azido group, an alkyl group which is optionally substituted with one or more halogen atoms, an alkenyl group which is optionally substituted with one or more halogen atoms, an aralkyl group which is optionally substituted with one or more halogen atoms, an alkoxy group which is optionally substituted with one or more halogen atoms, or an alkoxycarbonyl group which is optionally substituted with one or more halogen atoms;

which comprises reacting a tetrahydroquinazoline represented by the formula (I):

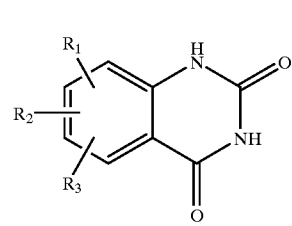

(I)

wherein $R_1$, $R_2$ and $R_3$ are as defined above with hexamethyldisilazane; and reacting the resultant product with a chloroalkanoate represented by the formula (II):

Cl—Z—CO—O—$R_6$ (II)

wherein Z and $R_6$ are as defined above, in the presence of an iodide of an alkali metal, followed by desilylation.

DETAILED DESCRIPTION OF THE PREFERRED EMBODIMENTS

Hereinafter, the present invention will be described in detail.

The substituents $R_1$ and $R_2$ in the tetrahydroquinazolines of formula (I), the starting material of the present invention, independently represent a hydrogen atom, a halogen atom, a nitro group, an azido group, an alkyl group which is optionally substituted with one or more halogen atoms, an alkenyl group which is optionally substituted with one or more halogen atoms, an aralkyl group which is optionally substituted with one or more halogen atoms, an alkoxy group which is optionally substituted with one or more halogen atoms, an alkoxycarbonyl group which is optionally substituted with one or more halogen atoms, an acyloxy group, or an amino group represented by $XNR_4R_5$ in which X represents a direct bond, an alkylene group or a carbonyl group, and N, $R_4$ and $R_5$ may form together a five- or six-membered heterocyclic ring which optionally contains another hetero atom which may be substituted or when X is a direct bond or an alkylene group, $R_4$ and $R_5$ independently represent an alkyl group or when X is a carbonyl group, $R_4$ and $R_5$ independently represent an acyloxy alkyl group.

Examples of the halogen atom include chlorine, bromine and fluorine.

Examples of the alkyl group which is optionally substituted with the halogen atom include lower alkyl groups such as methyl, ethyl, propyl, i-propyl, butyl, i-butyl, t-butyl, pentyl, i-pentyl and hexyl; monohalo lower alkyl groups such as chloromethyl, bromomethyl and chloropropyl; and dihalo lower alkyl groups such as 1,2-dichloroethyl, 1,2-dibromoethyl and 2,2-dichloroethyl; and trihalo lower alkyl groups such as trifluoromethyl.

Examples of the alkenyl group which is optionally substituted with the halogen atom include lower alkenyl groups such as 1-propenyl, 2-propenyl, 1-butenyl, 2-butenyl, 3-butenyl, 1-pentenyl, 2-pentenyl, 3-pentenyl and 4-pentenyl; monohalo lower alkenyl groups such as 3-chloro-1-propenyl and 3-chloro-1-butenyl; and dihalo lower alkenyl groups such as 3,4-dichloro-1-butenyl; and trihalo lower alkenyl groups such as 3,4,5-trichloro-1-pentenyl.

Examples of the aralkyl group which is optionally substituted with the halogen atom include benzyl, phenylethyl, 4-chlorobenzyl, 2,4-dichlorobenzyl and 2,4-dibromobenzyl.

Examples of the alkoxy group which is optionally substituted with the halogen atom include lower alkoxy groups such as methoxy, ethoxy, propoxy, i-propoxy, butoxy, i-butoxy, t-butoxy, pentyloxy, i-pentyloxy and hexyloxy; halogenated lower alkoxy groups such as chloromethoxy, bromomethoxy, 1-chloroethoxy, 2-chloroethoxy, 1-chloropropoxy, 2-chloropropoxy, 3-chloropropoxy, dichloromethoxy, dibromomethoxy, 1,2-dichloroethoxy, 2,2-dichloroethoxy, and trifluoromethoxy.

Examples of the alkoxycarbonyl group which is optionally substituted with the halogen atom include carbonyl groups substituted with an alkoxy group such as those exemplified above.

Examples of the acyloxy group include lower alkylcarbonyloxy groups such as acetoxy, propionyloxy, butylyloxy, i-butylyloxy, valeryloxy, i-valeryloxy and pivaloyloxy; and arylcarbonyloxy such as benzyloxy.

Examples of the alkylene group represented by X in the amino group $XNR_4R_5$ include lower alkylene groups such as methylene, dimethylene, trimethylene and tetramethylene.

Examples of $R_4$ and $R_5$ as the lower alkyl group in the amino group $XNR_4R_5$ include the same lower alkyl group as that exemplified above. In this case, specific examples of the amino group of $XNR_4R_5$ include dimethylamino, diethylamino, dipropylamino and dibutylamino.

Specific examples of the amino group of $XNR_4R_5$, in case that N, $R_4$ and $R_5$ form together to a five- or six-membered heterocyclic ring which optionally have another hetero atom, include pyrrolyl, 2H,4H-pyrrolyl, pyrrolidino, pyrazolyl, piperidino, piperazinyl, morpholino and imidazolyl.

When the other hetero atom in the heterocyclic ring is a nitrogen atom, it may be substituted. Examples of the substituent include alkyl groups such as those exemplified above, aralkyl groups such as those exemplified above, aralkyl groups which are optionally substituted by an alkoxy group and a phenylcarbonyl group which is optionally substituted by an alkoxy group.

Examples of the tetrahydroquinazolines (I) include
2,4-dioxo-1,2,3,4-tetrahydroquinazoline,
5-chloro-2,4-dioxo-1,2,3,4-tetrahydroquinazoline,
6-chloro-2,4-dioxo-1,2,3,4-tetrahydroquinazoline,
7-chloro-2,4-dioxo-1,2,3,4-tetrahydroquinazoline,
8-chloro-2,4-dioxo-1,2,3,4-tetrahydroquinazoline,
5-bromo-2,4-dioxo-1,2,3,4-tetrahydroquinazoline,
6-bromo-2,4-dioxo-1,2,3,4-tetrahydroquinazoline,
7-bromo-2,4-dioxo-1,2,3,4-tetrahydroquinazoline,
8-bromo-2,4-dioxo-1,2,3,4-tetrahydroquinazoline,
5-fluoro-2,4-dioxo-1,2,3,4-tetrahydroquinazoline,
6-fluoro-2,4-dioxo-1,2,3,4-tetrahydroquinazoline,
7-fluoro-2,4-dioxo-1,2,3,4-tetrahydroquinazoline,
8-fluoro-2,4-dioxo-1,2,3,4-tetrahydroquinazoline,
5,6-dichloro-2,4-dioxo-1,2,3,4-tetrahydroquinaizoline,
5,7-dichloro-2,4-dioxo-1,2,3,4-tetrahydroquinazoline,
5,8-dichloro-2,4-dioxo-1,2,3,4-tetrahydroquinazoline,
6,7-dichloro-2,4-dioxo-1,2,3,4-tetrahydroquinazoline,
6,8-dichloro-2,4-dioxo-1,2,3,4-tetrahydroquinazoline,
7,8-dichloro-2,4-dioxo-1,2,3,4-tetrahydroquinazoline,
5,6-dibromo-2,4-dioxo-1,2,3,4-tetrahydroquinazoline,
5,7-dibromo-2,4-dioxo-1,2,3,4-tetrahydroquinazoline,
5,8-dibromo-2,4-dioxo-1,2,3,4-tetrahydroquinazoline,
6,7-dibromo-2,4-dioxo-1,2,3,4-tetrahydroquinazoline,
6,8-dibromo-2,4-dioxo-1,2,3,4-tetrahydroquinazoline,
7,8-dibromo-2,4-dioxo-1,2,3,4-tetrahydroquinazoline,
5,6-difluoro-2,4-dioxo-1,2,3,4-tetrahydroquinazoline,
5,7-difluoro-2,4-dioxo-1,2,3,4-tetrahydroquinazoline,
5,8-difluoro-2,4-dioxo-1,2,3,4-tetrahydroquinazoline,
6,7-difluoro-2,4-dioxo-1,2,3,4-tetrahydroquinazoline,
7,8-difluoro-2,4-dioxo-1,2,3,4-tetrahydroquinazoline,
5-bromo-6-chloro-2,4-dioxo-1,2,3,4-tetrahydrocuinazoline,
5-bromo-7-chloro-2,4-dioxo-1,2,3,4-tetrahydrocuinazoline,
5-bromo-8-chloro-2,4-dioxo-1,2,3,4-tetrahydrocuinazoline,
6-bromo-5-chloro-2,4-dioxo-1,2,3,4-tetrahydroquinazoline,
6-bromo-7-chloro-2,4-dioxo-1,2,3,4-tetrahydroquinazoline,
6-bromo-8-chloro-2,4-dioxo-1,2,3,4-tetrahydroquinazoline,
7-bromo-5-chloro-2,4-dioxo-1,2,3,4-tetrahydroquinazoline,
7-bromo-6-chloro-2,4-dioxo-1,2,3,4-tetrahydroquinazoline,
7-bromo-8-chloro-2,4-dioxo-1,2,3,4-tetrahydrocquinazoline,
8-bromo-5-chloro-2,4-dioxo-1,2,3,4-tetrahydroquinazoline,
8-bromo-6-chloro-2,4-dioxo-1,2,3,4-tetrahydroquinazoline,
8-bromo-7-chloro-2,4-dioxo-1,2,3,4-tetrahydroquinazoline,
5,6,7-trichloro-2,4-dioxo-1,2,3,4-tetrahydroquinazoline,
5,6,8-trichloro-2,4-dioxo-1,2,3,4-tetrahydroquinazoline,
5,7,8-trichloro-2,4-dioxo-1,2,3,4-tetrahydroquinazoline,
6,7,8-trichloro-2,4-dioxo-1,2,3,4-tetrahydroquinazoline,
5,6,7-tribromo-2,4-dioxo-1,2,3,4-tetrahydroquinazoline,
5,6,8-tribromo-2,4-dioxo-1,2,3,4-tetrahydroquinazoline,
5,7,8-tribromo-2,4-dioxo-1,2,3,4-tetrahydroquinazoline,
6,7,8-tribromo-2,4-dioxo-1,2,3,4-tetrahydroquinazoline,
5,6,7-trifluoro-2,4-dioxo-1,2,3,4-tetrahydroquinazoline,
5,6,8-trifluoro-2,4-dioxo-1,2,3,4-tetrahydroquinazoline,
5,7,8-trifluoro-2,4-dioxo-1,2,3,4-tetrahydroquinazoline,
6,7,8-trifluoro-2,4-dioxo-1,2,3,4-tetrahydroquinazoline,
5-nitro-2,4-dioxo-1,2,3,4-tetrahydroquinazoline,
6-nitro-2,4-dioxo-1,2,3,4-tetrahydroquinazoline,
7-nitro-2,4-dioxo-1,2,3,4-tetrahydroquinazoline,
8-nitro-2,4-dioxo-1,2,3,4-tetrahydroquinazoline,
5-azido-2,4-dioxo-1,2,3,4-tetrahydroquinazoline,
6-azido-2,4-dioxo-1,2,3,4-tetrahydroquinazoline,
7-azido-2,4-dioxo-1,2,3,4-tetrahydroquinazoline,
8-azido-2,4-dioxo-1,2,3,4-tetrahydroquinazoline, 5-carboxy-2,4-dioxo-1,2,3,4-tetrahydroquinazoline,
6-carboxy-2,4-dioxo-1,2,3,4-tetrahydroquinazoline,
7-carboxy-2,4-dioxo-1,2,3,4-tetrahydroquinazoline,
8-carboxy-2,4-dioxo-1,2,3,4-tetrahydroquinazoline,
5-methyl-2,4-dioxo-1,2,3,4-tetrahydroquinazoline,
6-methyl-2,4-dioxo-1,2,3,4-tetrahydroquinazoline,
7-methyl-2,4-dioxo-1,2,3,4-tetrahydroquinazoline,
8-methyl-2,4-dioxo-1,2,3,4-tetrahydroquinazoline,
5-ethyl-2,4-dioxo-1,2,3,4-tetrahydroquinazoline,
6-ethyl-2,4-dioxo-1,2,3,4-tetrahydroquinazoline,
7-ethyl-2,4-dioxo-1,2,3,4-tetrahydroquinazoline,
8-ethyl-2,4-dioxo-1,2,3,4-tetrahydroquinazoline,
5-propyl-2,4-dioxo-1,2,3,4-tetrahydroquinazoline,
6-propyl-2,4-dioxo-1,2,3,4-tetrahydroquinazoline,
7-propyl-2,4-dioxo-1,2,3,4-tetrahydroquinazoline,
8-propyl-2,4-dioxo-1,2,3,4-tetrahydroquinazoline,
5-i-propyl-2,4-dioxo-1,2,3,4-tetrahydroquinazoline,
6-i-propyl-2,4-dioxo-1,2,3,4-tetrahydroquinazoline,
7-i-propyl-2,4-dioxo-1,2,3,4-tetrahydroquinazoline,
8-i-propyl-2,4-dioxo-1,2,3,4-tetrahydroquinazoline,
5-chloromethyl-2,4-dioxo-1,2,3,4-tetrahydroquinazoline,
6-chloromethyl-2,4-dioxo-1,2,3,4-tetrahydroquinazoline,
7-chloromethyl-2,4-dioxo-1,2,3,4-tetrahydroquinazoline,
8-chloromethyl-2,4-dioxo-1,2,3,4-tetrahydroquinazoline,
5-bromomethyl-2,4-dioxo-1,2,3,4-tetrahydroquinazoline,
6-bromomethyl-2,4-dioxo-1,2,3,4-tetrahydroquinazoline,
7-bromomethyl-2,4-dioxo-1,2,3,4-tetrahydroquinazoline,
8-bromomethyl-2,4-dioxo-1,2,3,4-tetrahydroquinazoline,
5-(1-chloroethyl)-2,4-dioxo-1,2,3,4-tetrahydroquinazoline,
6-(1-chloroethyl)-2,4-dioxo-1,2,3,4-tetrahydroquinazoline,
7-(1-chloroethyl)-2,4-dioxo-1,2,3,4-tetrahydroquinazoline,
8-(1-chloroethyl)-2,4-dioxo-1,2,3,4-tetrahydroquinazoline,
5-(2-chloroethyl)-2,4-dioxo-1,2,3,4-tetrahydroquinazoline,
6-(2-chloroethyl)-2,4-dioxo-1,2,3,4-tetrahydroquinazoline,
7-(2-chloroethyl)-2,4-dioxo-1,2,3,4-tetrahydroquinazoline,
8-(2-chloroethyl)-2,4-dioxo-1,2,3,4-tetrahydroquinazoline,
5-dichloromethyl-2,4-dioxo-1,2,3,4-tetrahydroquinazoline,
6-dichloromethyl-2,4-dioxo-1,2,3,4-tetrahydroquinazoline,
7-dichloromethyl-2,4-dioxo-1,2,3,4-tetrahydroquinazoline,
8-dichloromethyl-2,4-dioxo-1,2,3,4-tetrahydroquinazoline,
5-(1,2-dichloroethyl)-2,4-dioxo-1,2,3,4-tetrahydroquinazoline,
6-(1,2-dichloroethyl)-2,4-dioxo-1,2,3,4-tetrahydroquinazoline,
7-(1,2-dichloroethyl)-2,4-dioxo-1,2,3,4-tetrahydroquinazoline,
8-(1,2-dichloroethyl)-2,4-dioxo-1,2,3,4-tetrahydroquinazoline,
5-(2,2-dichloroethyl)-2,4-dioxo-1,2,3,4-tetrahydroquinazoline,
6-(2,2-dichloroethyl)-2,4-dioxo-1,2,3,4-tetrahydroquinazoline,
7-(2,2-dichloroethyl)-2,4-dioxo-1,2,3,4-tetrahydroquinazoline,
8-(2,2-dichloroethyl)-2,4-dioxo-1,2,3,4-tetrahydroquinazoline,
5-(2,2-dichloroethyl)-2,4-dioxo-1,2,3,4-tetrahydroquinazoline,
5-ethenyl-2,4-dioxo-1,2,3,4-tetrahydroquinazoline,
6-ethenyl-2,4-dioxo-1,2,3,4-tetrahydroquinazoline,
7-ethenyl-2,4-dioxo-1,2,3,4-tetrahydroquinazoline,
8-ethenyl-2,4-dioxo-1,2,3,4-tetrahydroquinazoline,
5-(1-propenyl)-2,4-dioxo-1,2,3,4-tetrahydroquinazoline,
6-(1-propenyl)-2,4-dioxo-1,2,3,4-tetrahydroquinazoline,
7-(1-propenyl)-2,4-dioxo-1,2,3,4-tetrahydroquinazoline,
8-(1-propenyl)-2,4-dioxo-1,2,3,4-tetrahydroquinazoline,
5-(2-propenyl)-2,4-dioxo-1,2,3,4-tetrahydroquinazoline,
6-(2-propenyl)-2,4-dioxo-1,2,3,4-tetrahydroquinazoline,
7-(2-propenyl)-2,4-dioxo-1,2,3,4-tetrahydroquinazoline,
8-(2-propenyl)-2,4-dioxo-1,2,3,4-tetrahydroquinazoline,
5-(1-butenyl)-2,4-dioxo-1,2,3,4-tetrahydroquinazoline,
6-(1-butenyl)-2,4-dioxo-1,2,3,4-tetrahydroquinazoline,
7-(1-butenyl)-2,4-dioxo-1,2,3,4-tetrahydroquinazoline,
8-(1-butenyl)-2,4-dioxo-1,2,3,4-tetrahydroquinazoline,
5-(1-pentenyl)-2,4-dioxo-1,2,3,4-tetrahydroquinazoline,
6-(1-pentenyl)-2,4-dioxo-1,2,3,4-tetrahydroquinazoline,
7-(1-pentenyl)-2,4-dioxo-1,2,3,4-tetrahydroquinazoline,
8-(1-pentenyl)-2,4-dioxo-1,2,3,4-tetrahydroquinazoline,
5-(3-chloro-1-propenyl)-2,4-dioxo-1,2,3,4-tetrahydroquinazoline, 6-(3-chloro-1-propenyl)-2,4-dioxo-1,2,3,4-tetrahydroquinazoline, 7-(3-chloro-1-propenyl)-2,4-dioxo-1,2,3,4-tetrahydroquinazoline, 8-(3-chloro-1-propenyl)-2,4-dioxo-1,2,3,4-tetrahydroquinazoline, 5-(3,4-dichloro-1-butenyl)-2,4-dioxo-1,2,3,4-tetrahydroquinazoline,
6-(3,4-dichloro-1-butenyl)-2,4-dioxo-1,2,3,4-tetrahydroquinazoline, 7-(3,4-dichloro-1-buter.yl)-2,4-dioxo-1,2,3,4-tetrahydroquinazoline, 8-(3,4-dichloro)-1-butenyl)-2,4-dioxo-1,2,3,4-tetrahydroquinazoline,
5-methoxy-2,4-dioxo-1,2,3,4-tetrahydroquinazoline,
6-methoxy-2,4-dioxo-1,2,3,4-tetrahydroquinazoline,
7-methoxy-2,4-dioxo-1,2,3,4-tetrahydroquinazoline,
8-methoxy-2,4-dioxo-1,2,3,4-tetrahydroquinazoline,
5-ethoxy-2,4-dioxo-1,2,3,4-tetrahydroquinazoline,
6-ethoxy-2,4-dioxo-1,2,3,4-tetrahydroquinazoline,
7-ethoxy-2,4-dioxo-1,2,3,4-tetrahydroquinazoline,
8-ethoxy-2,4-dioxo-1,2,3,4-tetrahydroquinazoline,
5-propoxy-2,4-dioxo-1,2,3,4-tetrahydroquinazoline,
6-propoxy-2,4-dioxo-1,2,3,4-tetrahydroquinazoline,
7-propoxy-2,4-dioxo-1,2,3,4-tetrahydroquinazoline,
8-propoxy-2,4-dioxo-1,2,3,4-tetrahydroquinazoline,
5-i-propoxy-2,4-dioxo-1,2,3,4-tetrahydroquinazoline,
6-i-propoxy-2,4-dioxo-1,2,3,4-tetrahydroquinazoline,
7-i-propoxy-2,4-dioxo-1,2,3,4-tetrahydroquinazoline,
8-i-propoxy-2,4-dioxo-1,2,3,4-tetrahydroquinazoline,
5-t-butoxy-2,4-dioxo-1,2,3,4-tetrahydroquinazoline,
6-t-butoxy-2,4-dioxo-1,2,3,4-tetrahydroquinazoline,
7-t-butoxy-2,4-dioxo-1,2,3,4-tetrahydroquinazoline,
8-t-butoxy-2,4-dioxo-1,2,3,4-tetrahydroquinazoline,
5-chloromethoxy-2,4-dioxo-1,2,3,4-tetrahydroquinazoline,
6-chloromethoxy-2,4-dioxo-1,2,3,4-tetrahydroquinazoline,
7-chloromethoxy-2,4-dioxo-1,2,3,4-tetrahydroquinazoline,
8-chloromethoxy-2,4-dioxo-1,2,3,4-tetrahydroquinazoline,
5-bromomethoxy-2,4-dioxo-1,2,3,4-tetrahydroquinazoline,
6-bromomethoxy-2,4-dioxo-1,2,3,4-tetrahydroquinazoline,
7-bromomethoxy-2,4-dioxo-1,2,3,4-tetrahydroquinazoline,
8-bromomethoxy-2,4-dioxo-1,2,3,4-tetrahydroquinazoline,
5-(2-chloroethoxy)-2,4-dioxo-1,2,3,4-tetrahydroquinazoline,
6-(2-chloroethoxy)-2,4-dioxo-1,2,3,4-tetrahydroquinazoline,
7-(2-chloroethoxy)-2,4-dioxo-1,2,3,4-tetrahydroquinazoline,
8-(2-chloroethoxy)-2,4-dioxo-1,2,3,4-tetrahydroquinazoline,
5-(1-chloropropoxy)-2,4-dioxo-1,2,3,4-tetrahydroquinazoline,
6-(1-chloropropoxy)-2,4-dioxo-1,2,3,4-tetrahydroquinazoline,
7-(1-chloropropoxy)-2,4-dioxo-1,2,3,4-tetrahydroquinazoline,
8-(1-chloropropoxy)-2,4-dioxo-1,2,3,4-tetrahydroquinazoline,
5-(2-chloropropoxy)-2,4-dioxo-1,2,3,4-tetrahydroquinazoline, 6-(2-chloropropoxy)-2,4-dioxo-1,2,3,4-tetrahydroquinazoline,
7-(2-chloropropoxy)-2,4-dioxo-1,2,3,4-tetrahydroquinazoline,
8-(2-chloropropoxy)-2,4-dioxo-1,2,3,4-tetrahydroquinazoline,
5-(3-chloropropoxy)-2,4-dioxo-1,2,3,4-tetrahydroquinazoline,
6-(3-chloropropoxy)-2,4-dioxo-1,2,3,4-tetrahydroquinazoline,
7-(3-chloropropoxy)-2,4-dioxo-1,2,3,4-tetrahydroquinazoline,
8-(3-chloropropoxy)-2,4-dioxo-1,2,3,4-tetrahydroquinazoline,
5-dichloromethoxy-2,4-dioxo-1,2,3,4-tetrahydroquinazoline,
6-dichloromethoxy-2,4-dioxo-1,2,3,4-tetrahydroquinazoline,
7-dichloromethoxy-2,4-dioxo-1,2,3,4-tetrahydroquinazoline,
8-dichloromethoxy-2,4-dioxo-1,2,3,4-tetrahydroquinazoline,
5-dibromomethoxy-2,4-dioxo-1,2,3,4-tetrahydroquinazoline,
6-dibromomethoxy-2,4-dioxo-1,2,3,4-tetrahydroquinazoline,
7-dibromomethoxy-2,4-dioxo-1,2,3,4-tetrahydroquinazoline,
8-dibromomethoxy-2,4-dioxo-1,2,3,4-tetrahydroquinazoline,
5-trifluoromethoxy-2,4-dioxo-1,2,3,4-tetrahydroquinazoline,
6-trifluoromethoxy-2,4-dioxo-1,2,3,4-tetrahydroquinazoline,
7-trifluoromethoxy-2,4-dioxo-1,2,3,4-tetrahydroquinazoline,
8-trifluoromethoxy-2,4-dioxo-1,2,3,4-tetrahydroquinazoline,
5-chloromethoxycarbonyl-2,4-dioxo-1,2,3,4-tetrahydroquinazoline, 6-chloromethoxycarbonyl-2,4-dioxo-1,2,3,4-tetrahydroquinazoline, 7-chloromethoxycarbonyl-2,4-dioxo-1,2,3,4-tetrahydroquinazoline, 8-chloromethoxycarbonyl-2,4-dioxo-1,2,3,4-tetrahydroquinazoline,
5-bromomethoxycarbonyl-2,4-dioxo-1,2,3,4-tetrahydroquinazoline,
6-bromomethoxycarbonyl-2,4-dioxo-1,2,3,4-tetrahydroquinazoline,
7-bromomethoxycarbonyl-2,4-dioxo-1,2,3,4-tetrahydroquinazoline,
8-bromomethoxycarbonyl-2,4-dioxo-1,2,3,4-tetrahydroquinazoline,
5-(1-chloroethoxycarbonyl)-2,4-dioxo-1,2,3,4-tetrahydroquinazoline, 6-(1-chloroethoxycarbonyl)-2,4-dioxo-1,2,3,4-tetrahydroquinazoline, 7-(1-chloroethoxycarbonyl)-2,4-dioxo-1,2,3,4-tetrahydroquinazoline, 8-(1-chloroethoxycarbonyl)-2,4-dioxo-1,2,3,4-tetrahydroquinazoline, 5-(2-chloroethoxycarbonyl)-2,4-dioxo-1,2,3,4-tetrahydroquinazoline, 6-(2-chloroethoxycarbonyl)-2,4-dioxo-1,2,3,4-tetrahydroquinazoline, 7-(2-chloroethoxycarbonyl)-2,4-dioxo-1,2,3,4-tetrahydroquinazoline, 8-(2-chloroethoxycarbonyl)-2,4-dioxo-1,2,3,4-tetrahydroquinazoline, 5-(1-chloropropoxycarbonyl)-2,4-dioxo-1,2,3,4-tetrahydroquinazoline, 6-(1-chloropropoxycarbonyl)-2,4-dioxo-1,2,3,4-tetrahydroquinazoline, 7-(1-chloropropoxycarbonyl)-2,4-dioxo-1,2,3,4-tetrahydroquinazoline, 8-(1-chloropropoxycarbonyl)-2,4-dioxo-1,2,3,4-tetrahydroquinazoline, 5-dichloromethoxycarbonyl-2,4-dioxo-1,2,3,4-tetrahydroquinazoline, 6-dichloromethoxycarbonyl-2,4-dioxo-1,2,3,4-tetrahydroquinazoline, 7-dichloromethoxycarbonyl-2,4-dioxo-1,2,3,4-tetrahydroquinazoline, 8-dichloromethcxycarbonyl-2,4-dioxo-1,2,3,4-tetrahydroquinazoline,
5-dibromcmethoxycarbonyl-2,4-dioxo-1,2,3,4-tetrahydroquinazoline, 6-dibromomethoxycarbonyl-2,4-dioxo-1,2,3,4-tetrahydroquinazoline, 7-dibromomethoxycarbony-l-2,4-dioxo-1,2,3,4-tetrahydroquinazoline, 8-dibromomethox.ycarbonyl-2,4-dioxo-1,2,3,4-tetrahydroquinazoline, 5-(1,2-dichloroethoxycarbonyl)-2,4-dioxo-1,2,3,4-tetrahydroquinazoline, 6-(1,2-dichloroethoxycarbonyl)-2,4-dioxo-1,2,3,4-tetrahydroquinazoline, 7-(1,2-dichloroethoxycarbonyl)-2,4-dioxo-1,2,3,4-tetrahydroquinazoline, 8-(1,2-dichloroethoxycarbonyl)-2,4-dioxo-1,2,3,4-tetrahydroquinazoline, 5-(2,2-dichloroethoxycarbonyl)-2,4-dioxo-1,2,3,4-tetrahydroquinazoline, 6-(2,2-dichloroethoxycarbonyl)-2,4-dioxo-1,2,3,4-tetrahydroquinazoline, 7-(2,2-dichloroethoxycarbonyl)-2,4-dioxo-1,2,3,4-tetrahydroquinazoline, 8-(2,2-dichloroethoxycE-rbonyl)-2,4-dioxo-1,2,3,4-tetrahydroquinazoline, 5-trifluoromethoxycarbonyl-2,4-dioxo-1,2,3,4-tetrahydroquinazoline, 6-trifluoromethoxycarbonyl-2,4-dioxo-1,2,3,4-tetrahydroquinazoline, 7-trifluoromethoxycarbonyl-2,4-dioxo-1,2,3,4-tetrahydroquinazoline, 8-trifluoromethoxycarbonyl-2,4-dioxo-1,2,3,4-tetrahydroquinazoline,
7,8-dimethyl-2,4-dioxo-1,2,3,4-tetrahydroquinazoline,
7,8-diethyl-2,4-dioxo-1,2,3,4-tetrahydroquinazoline,
6-benzyl-2,4-dioxo-1,2,3,4-tetrahydroquinazoline,
6-(2-phenylethyl)-2,4-dioxo-1,2,3,4-tetrahydrcquinazoline,
6-(4-chlorobenzyl)-2,4-dioxo-1,2,3,4-tetrahydroquinazoline,
6-(2,4-dichlorobenzyl)-2,4-dioxo-1,2,3,4-tetrahydroquinazoline,
6-(2,4-dibromobenzyl)-2,4-dioxo-1,2,3,4-tetrahydroquinazoline,
5,6-dimethoxy-2,4-dioxo-1,2,3,4-tetrahydroquinazoline,
6,8-dimethoxy-2,4-dioxo-1,2,3,4-tetrahydroquinazoline,
5,8-dipropoxy-2,4-dioxo-1,2,3,4-tetrahydroquinazoline,
6-(N,N-dimethylamino)-2,4-dioxo-1,2,3,4-tetrahydroquinazoline,
6-(N,N-diethylamino)-2,4-dioxo-1,2,3,4-tetrahydroquinazoline,
6-(N,N-dimethylamino)-2,4-dioxo-1,2,3,4-tetrahydroquinazoline,
6-(N,N-dibutylamino)-2,4-dioxo-1,2,3,4-tetrahydroquinazoline,
6-(1-pyrrolyl)-2,4-dioxo-1,2,3o4-tetrahydroquinnazoline,
6-(1-imidazolyl)-2,4-dioxo-1,2,3,4-tetrahydroquinazoline,
6-(1-pyrazolyl)-2,4-dioxo-1,2,3,4-tetrahydroquinazoline,
6-(2H,4H-pyrrolyl)-2,4-dioxo-1,2,3,4-tetrahydroquinazoline,
6-piperidino-2,4-dioxo-1,2,3,4-tetrahydroquinazoline,
6-morpholino-2,4-dioxo-1,2,3,4-tetrahydroquinazoline,
6-(4-methylpiperazinyl)-2,4-dioxo-1,2,3,4-tetrahydroquinazoline, 6-(4-chloromethylpiperazinyl)-2,4-dioxo-1,2,3,4-tetrahydroquinazoline, 6-(4-benzylpiperazinyl)-2,4-dioxo-1,2,3,4-tetrahydroquinazoline, 6-(4-(3-methoxybenzyl)piperazinyl)-2,4-dioxo-1,2,3,4-tetrahydroquinazoline, 6-(4-(phenylcarbonyl) piperazinyl)-2,4-dioxo-1,2,3,4-tetrahydroquinazoline, 6-(4-(3,4-dimethoxyphenylcarbonyl) piperazinyl)-2,4-dioxo-1,2,3,4-tetrahydroquinazoline,
6-(1-pyrrolylmethyl)-2,4-dioxo-1,2,3,4-tetrahydroquinazoline,
6-morpholinomethyl-2,4-dioxo-1,2,3,4-tetrahydroquinazoline,
7-(4-piperazinylmethyl)-2,4-dioxo-1,2,3,4-tetrahydroquinazoline, 6-(4-(3-phenylcarbonylpropyl) piperazinylcarbonyl)-2,4-dioxo-1,2,3,4-tetrahydroquinazoline, 7-(4-methylpiperazinylcarbonyl)-2,4-dioxo-1,2,3,4-tetrahydroquinazoline, 6-(4-benzylpiperidinocarbonyl)-2,4-dioxo-1,2,3,4-tetrahydroquinazoline,
6-acetoxy-2,4-dioxo-1,2,3,4-tetrahydroquinazoline,
6-propionyloxy-2,4-dioxo-1,2,3,4-tetrahydroquinazoline,
6-butyloxy-2,4-dioxo-1,2,3,4-tetrahydroquinazoline,
6-i-butyloxy-2,4-dioxo-1,2,3,4-tetrahydroquinazoline,
6-valeryloxy-2,4-dioxo-1,2,3,4-tetrahydroquinazoline,
6-pivaloyloxy-2,4-dioxo-1,2,3,4-tetrahydroquirazoline,
6-benzoyloxy-2,4-dioxo-1,2,3,4-tetrahydroquinazoline,
5,7-dimethyl-6-propionyloxy-2,4-dioxo-1,2,3,4-tetrahydroquinazoline and 8-chloro-5,6-dimethcoxy-2,4-dioxo-1,2,3,4-tetrahydroquinazoline.

The hexamethyldisilazane silylation agent may be used in a 0.5 to 10 fold molar amount, preferably from about 1 to 5 fold molar amount, relative to the amount of the tetrahydro quinazolines of formula (I).

The silylation reaction may be carried out in a solvent at from room temperature to the reflux temperature of the solvent. The reaction can be accelerated by carrying it out in the presence of a salt such as ammonium sulfate, ammonium chloride, quanidine hydrochloride or pyridine hydrochloride, or of a mineral acid such as sulfuric acid or hydrochloric acid. In this case, the salt, the mineral acid or the like may be used in a 0.01 to 1 fold molar amount, preferably about 0.05 to 0.5 fold molar amount, relative to the amount of the tetrahydroquinazolines of formula (I).

The silylation reaction is preferably carried out under a reduced pressure and/or in an inert gas flow. By carrying out the reaction under a reduced pressure and/or in an inert gas flow, the reaction time can be shorten and/or reduction of the amount of hexamethyldisilazane can be attained. Range of the reduced pressure does not have a definite limit, but the range is usually from about 750 mm Hg, a slightly reduced pressure, to a pressure where the reaction solvent boils at room temperature, preferably from about 600 mm Hg to a pressure where the reaction solvent boils at room temperature, and more preferably the reduced pressure is about the pressure where the reaction solvent boils at room temperature. The inert gas may be any one which does not disturb the reaction, and includes nitrogen, helium, argon and the like. The inert gas may be a mixture of two or more gases. The amount of flow of the inert gas is not limited. Usually, the greater the amount, the more effective. Considering economical reasons etc., usually about 5–1000 ml/min., preferably 10–500 ml/min., is adopted relative to 1 l of reaction vessel.

The solvent for the silylation reaction may be any suitable solvent provided it does not inhibit the reaction. Examples thereof include aromatic hydrocarbons such as benzene, toluene and xylene, chlorobenzene, o-dichlorobenzene, m-dichlorobenzene and bromobenzene; hydrocarbon halides such as dichloromethane and chloroform; ether solvents such as tetrahydrofuran and dioxane; and mixtures thereof. The solvent may be used in a 0.5 to 10 fold amount by weight, preferably about 1 to 5 fold amount by weight, relative to the amount of the tetrahydroquinazolines of formula (I).

The resultant silylated product may be used in the following step after isolation from the reaction mass, or may be subjected to the following step as it is.

After silylation, the resultant product is reacted with the chloroalkanoate of formula (II) in the presence of the iodide of the alkaline metal, followed by desilylation. The substituent Z in the chloroalkanoate of formula (II) is a methylene group which is optionally substituted with an alkyl group and $R_6$ is an alkyl group or an aralkyl group. Examples of the alkyl group include a lower alkyl group as that exemplified above. Examples of the methylene group which is optionally substituted with an alkyl group include methylene and methylmethylene, preferably methylene. Examples of the aralkyl group include aralkyl group whose aromatic ring is optionally substituted with a nitro group, such as benzyl, 4-nitrobenzyl, phenylethyl, benzhydryl and trityl.

As the chloroalkanoate of formula (II), those wherein $R_6$ is a lower alkyl group are preferred. Examples include methyl chloroacetate, ethyl chloroacetate, propyl chloroacetate, t-butyl chloroacetate and ethyl 2-chloropropionate.

The chloroalkanoate of formula (II) may be used in a 1 to 5 fold molar amount relative to the amount of the tetrahydroquinazolines of formula (I).

The present invention is characterized by reacting the above-described chloroalkanoate (II) in the presence of the iodide of the alkaline metal. Examples of the iodide of the alkaline metal include potassium iodide, sodium iodide and lithium iodide. Among them, potassium iodide and sodium iodide are preferably used.

The iodide of the alkali metal may be used in a 0.001 to 1 fold molar amount, preferably from about 0.1 to 1 fold molar amount, relative to the amount of the tetrahydroquinazolines of formula (I).

The solvent for the reaction with the chloroalkanoate (II) may be any one which does not inhibit the reaction. Examples thereof include aromatic hydrocarbon such as benzene, toluene and xylene, chlorobenzene, o-dichlorobenzene, m-dichlorobenzene and bromobenzene; hydrocarbon halides such as dichloromethane and chloroform; ether solvent such as tetrahydrofuran and dioxane; and a mixture thereof. Among them, aromatic hydrocarbons are preferred. Particularly, aromatic hydrocarbons substituted with halogen such as chlorobenzene, o-dichlorobenzene, m-dichlorobenzene and bromohenzene are preferred. By using aromatic hydrocarbons substituted with halogen as the reaction solvent, the productivity of facilities can be improved by shortening the reaction time. The solvent is normally used in a 0.5 to 10 fold amount by weight, preferably about 1 to 5 fold amount by weight, relative to the tetrahydroquinazolines (I) used in the reaction.

The reaction temperature with the chlorcalkanoate (II) may be from about 0° C. to a boiling point of the solvent, preferably from about 80° C. to a boiling point of the solvent. As progress of the reaction, contents which have a lower boiling point, such as trimethylchlorosilane, is generated. The reaction can be carried out while distilling off the contents which have a lower boiling point .

The desilylation can be carried out by, for example, adding water or an alcohol such as methanol, ethanol and i-propanol. These are normally used in a 2 to 30 fold molar amount, preferably from about 10 to 20 fold molar amount, relative to the amount of the tetrahydroquinazolines of formula (I).

Thus, 1-substituted tetrahydroquinazolines of formula (III), the objective product, are produced. When the objective product is deposited as a solid in the reaction mass, it can be removed from the reaction mass by, for example, filtration. When the objective product is dissolved in the reaction mass, it can be removed from the reaction mass by, for example, distilling off the solvent, adding water, extracting with an organic solvent and distilling off the organic solvent.

The 1-substituted tetrahydroquinazolines of formula (III) can also be removed in the form of a salt, for example, with an inorganic base, such as an alkali metal salt, alkaline earth metal salt and ammonium salt; salt with an organic base, such as an organic amine salt; addition salt with an inorganic acid, such as hydrochloride, hydrobromide, sulfate and phosphate; and addition salt with an organic acid, such as formate, acetate, trifluoroacetate, maleate, tartrate, methanesulfonate, benzenesulfonate and toluenesulfonate according to known processes.

The resultant 1-substituted tetrahydroquinazolines of formula (III) or salt thereof can also be further purified, for example, by recrystallization or various chromatographic treatments.

According to the present invention, the 1-substituted tetrahydroquinazolines of formula (III) can be produced with high yield by reacting with the chloroalkanoate of formula (II) in the presence of the iodide of the alkaline metal.

The following Examples further illustrate the present invention in detail but are not to be construed to limit the scope thereof.

EXAMPLE 1

A mixture of 17.3 g of toluene, 10 g of 7-chloro-2,4-dioxo-1,2,3,4-tetrahydroquinazoline, 19.7 g of hexamethyldisilazane and 1 g of ammonium sulfate was refluxed for 2 hours with stirring, and then excess hexamethyldisilazane and toluene (26.3 g) were distilled off at 55° C. under a reduced pressure of 20 to 30 mmHg.

To this were added 8.45 g of potassium iodide and 27.6 g of ethyl chloroacetate and, after stirring continuously at 110 to 120° C. for 12 hours, 40 g of ethanol was added and the mixture was refluxed for 1 hour. After cooling to room temperature, the deposited crystals were filtered, washed with ethanol and water, and then dried to obtain 13.9 g of crystals.

The content of 2-(7-chloro-2,4-dioxo-1,2,3,4-tetrahydroquinazolin-1-yl)ethyl acetate in this was 100%. (yield 96.4%)

EXAMPLE 2

According to the same manner as that described in Example 1 except that the amount of hexamethyldisilazane was changed to 38.2 g, the time of reflux was changed to 5 hours, the amount of toluene distilled off was 40.8 g, the amount of potassium iodide was changed to 1.69 g and time of stirring was changed to 32 hours, the reaction was carried out to obtain 14.1 g of crystals.

The content of 2-(7-chloro-2,4-dioxo-1,2,3,4-tetrahydroquinazolin-1-yl)ethyl acetate in this was 95.5%. (yield 93.7%)

Comparative Example 1

According to the same manner as that described in Example 1 except that potassium iodide was not used, the reaction was carried out to obtain 11.5 g of crystals.

The content of 2-(7-chloro-2,4-dioxo-1,2,3,4-tetrahydroquinazolin-1-yl)ethyl acetate in this was 56.8%. (yield 45.7%)

EXAMPLE 3

A mixture of 17 g of o-dichlorobenzene, 1.0 g of 7-chloro-2,4-dioxo-1,2,3,4-tetrahydroquinazoline, 19 g of hexamethyldisilazane and 1 g of ammonium sulfate was stirred at 120 for 10 hours, and then excess hexamethyldisilazane was distilled off at 55° C. under a reduced pressure of 50 mmHg.

To this were added 1.6 g of potassium iodide and 27 g of ethyl chloroacetate and the resultant mixture was stirred continuously at 130° C. to carry out the reaction. Progress of the reaction was checked with a high-speed liquid chromatography. It took 16 hours that the remaining amount of 7-chloro-2,4-dioxo-1,2,3,4-tetrahydroquinazoline in the reaction mass became 1% or less. The yield of 2-(7-chloro-2,4-dioxo-1,2,3,4-tetrahydroquinazolin-1-yl)ethyl acetate was 95%.

EXAMPLE 4

According to the same manner as that described in Example 3 except that 17 g of 0-dichlorobenzene was replaced with 17 g of chlorobenzene and the reaction temperature after adding ethyl chloroacetate was changed from 130 to 120. It took 21 hours that the remaining amount of 7-chloro-2,4-dioxo-1,2,3,4-tetrahydroquinazoline in the reaction mass became 1% or less. The yield of 2-(7-chloro-2,4-dioxo-1,2,3,4-tetrahydroquinazolin-1-yl)ethyl acetate was 91%.

EXAMPLE 5

According to the same manner as that described in Example 3 except that 17 g of 0-dichlorobenzene was replaced with 17 g of toluene, excess hexamethyldisilazane was distilled off at 25° C. under a reduced pressure of 20 mmHg and the reaction temperature after adding ethyl chloroacetate was changed from 130 to 120. It took 57 hours that the remaining amount of 7-chloro-2,4-dioxo-1,2,3,4-tetrahydroquinazoline in the reaction mass became 1% or less. The yield of 2-(7-chloro-2,4-dioxo-1,2,3,4-tetrahydroquinazolin-1-yl)ethyl acetate was 90%.

EXAMPLE 6

A mixture of 40 g of o-dichlorobenzene, 20 g of 7-chloro-2,4-dioxo-1,2,3,4-tetrahydroquinazoline, 30 g of hexamethyldisilazane and 2 g of ammonium sulfate was stirred at 150 for 3 hours, and then excess hexamethyldisilazane was distilled off at 55° C. under a reduced pressure of 10 mmHg.

To this were added 3.4 g of potassium iodide and 37 g of ethyl chloroacetate and the resultant mixture was stirred continuously at 130° C. to carry out the reaction, while distilling off the lower boiling point content such as trimethylchlorosilane generated with progress of the reaction. It took 21 hours that the remaining amount of 7-chloro-2,4-dioxo-1,2,3,4-tetrahydroquinazoline in the reaction mass became 1% or less.

After cooling to room temperature, ethyl acetate and water was added to deposit crystals. The deposited crystals were filtered, washed with methanol and water, and then dried to obtain 27.4 g of crystals.

The content of 2-(7-chloro-2,4-dioxo-1,2,3,4-tetrahydroquinazolin-1-yl)ethyl acetate in this was 98%. (yield 94%)

EXAMPLE 7

According to the same manner as that described in Example 6 except that excess hexamethyldisilazane and the contents which have a lower boiling point such as trimethylchlorosilane were not distilled off. It took 25 hours that the remaining amount of 7-chloro-2,4-dioxo-1,2,3,4-tetrahydroquinazoline in the reaction mass became 1% or less.

Same after-treatment as that in Example 6 was carried out to obtain 25.7 g of crystals.

The content of 2-(7-chloro-2,4-dioxo-1,2,3,4-tetrahydroquinazolin-1-yl)ethyl acetate in this was 97%. (yield 88%)

EXAMPLE 8

A mixture of 82 g of o-dichlorobenzene, 20.4 g of 7-chloro-2,4-dioxo-1,2,3,4-tetrahydroquinazoline, 16.4 g of hexamethyldisilazane and 0.8 g of sulfuric acid was stirred at 140 for 7 hours in a 300 ml vessel, while flowing nitrogen gas at 20 ml/min. Then, excess hexamethyldisilazane and a part of o-dichlorobenzene were distilled off under a reduced pressure.

To this were added 2.9 g of sodium iodide and 17.7 g of ethyl chloroacetate and, after stirring continuously at 111–132° C. for 30 hours, a mixture of ethyl acetate and methanol was added to deposit crystals. The deposited crystals were filtered, washed with methanol and water, and then dried to obtain 25.1 g of crystals.

The content of 2-(7-chloro-2,4-dioxo-1,2,3,4-tetrahydroquinazolin-1-yl)ethyl acetate in this was 99%. (yield 92%)

EXAMPLE 9

A mixture of 596 g of o-dichlorobenzene, 151 g of 7-chloro-2,4-dioxo-1,2,3,4-tetrahydroquinazoline, 134 g of hexamethyldisilazane and 6 g of sulfuric acid was stirred at 100–140 for 12 hours under a reduced pressure of 360–200 mm Hg. Then, excess hexamethyldisilazane and a part of o-dichlorobenzene were distilled off under a reduced pressure.

To this were added 23 g of sodium iodide and 185 g of ethyl chloroacetate and, after stirring continuously at 135° C. for 24 hours, a mixture of ethyl acetate and methanol was added to deposit crystals. The deposited crystals were filtered, washed with methanol and water, and then dried to obtain 207.7 g of crystals.

The content of 2-(7-chloro-2,4-dioxo-1,2,3,4-tetrahydroquinazolin-1-yl)ethyl acetate in this was 97%. (yield 95%)

What is claimed is:

1. A process for producing a 1-substituted tetrahydroquinazoline represented by the formula (III):

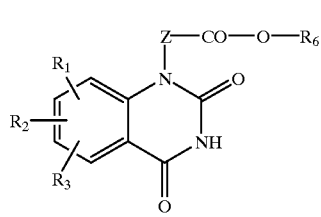

wherein
Z represents a methylene group;
$R_6$ represents an alkyl group or an aralkyl group;
$R_1$ and $R_2$ independently represent a hydrogen atom, a halogen atom, a nitro group, an azido group, an alkyl group, an alkenyl group, an aralkyl group, an alkoxy group, an alkoxycarbonyl group, an acyloxy group, or an amino group represented by $XNR_4R_5$ in which X represents a direct bond, an alkylene group or a carbonyl group, and N, $R_4$ and $R_5$ may form together a five- or six-membered heterocyclic ring which optionally contains another hetero atom in addition to the N atom or when X is a direct bond or an alkylene group, $R_4$ and $R_5$ independently may additionally represent an alkyl group or when X is a carbonyl group, $R_4$ and $R_5$ independently may additionally represent an acyloxy alkyl group; and
$R_3$ represents a hydrogen atom, a halogen atom, a nitro group, an azido group, an alkyl group, an alkenyl group, an aralkyl group, an alkoxy group, or an alkoxycarbonyl group, which comprises reacting a tetrahydroquinazoline represented by the formula (I):

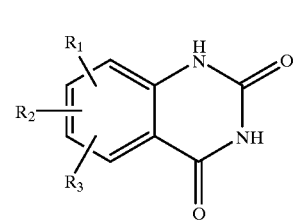

wherein $R_1$, $R_2$ and $R_3$ are as defined above, with hexamethyldisilazane; and reacting the resultant product with a chloroalkanoate represented by the formula (II):

wherein Z and $R_6$ are as defined above in the presence of an iodide of an alkali metal, followed by desilylation.

2. A process for producing a 1-substituted tetrahydroquinazoline represented by the formula (III):

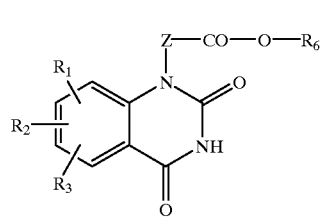

wherein
Z represents a methylene group or a methylene group which is substituted by an alkyl group;
$R_6$ represents an alkyl group or an aralkyl group;
$R_1$ and $R_2$ independently represent a hydrogen atom, a halogen atom, a nitro group, an azido group, an alkyl group, an alkyl group substituted by one or more halogen atoms, an alkenyl group, an alkenyl group substituted by one or more halogen atoms, an aralkyl group, an aralkyl group substituted by one or more halogen atoms, an alkoxy group, an alkoxy group substituted by one or more halogen atoms, an alkoxycarbonyl group, an alkoxycarbonyl group substituted by one or more halogen atoms, an acyloxy group, or an amino group represented by $XNR_4R_5$ in which X represents a direct bond, an alkylene group or a carbonyl group, and N, $R_4$ and $R_5$ may form together a five- or six-membered heterocyclic ring which optionally contains another hetero atom in addition to the N atom or when X is a direct bond or an alkylene group, $R_4$ and $R_5$ independently may additionally represent an alkyl group or when X is a carbonyl group, $R_4$ and $R_5$ independently may additionally represent an acyloxy alkyl group;

$R_3$ represents a hydrogen atom, a halogen atom, a nitro group, an azido group, an alkyl group, an alkyl group substituted by one or more halogen atoms, an alkenyl group, an alkenyl group substituted by one or more halogen atoms, an aralkyl group, an aralkyl group substituted by one or more halogen atoms, an alkoxy group, an alkoxy group substituted by one or more halogen atoms, an alkoxycarbonyl group, or an alkoxycarbonyl group substituted by one or more halogen atoms, which comprises reacting a tetrahydroquinazoline represented by the formula (I):

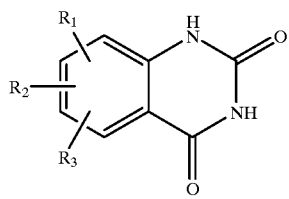

(I)

wherein $R_1$, $R_2$ and $R_3$ are as defined above, with hexamethyldisilazane; and reacting the resultant product with a chloroalkanoate represented by the formula (II):

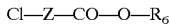

Cl—Z—CO—O—$R_6$ (II)

wherein Z and $R_6$ are as defined above in the presence of an iodide of an alkali metal, followed by desilylation.

3. A process for producing a 1-substituted tetrahydroquinazoline represented by the formula (III):

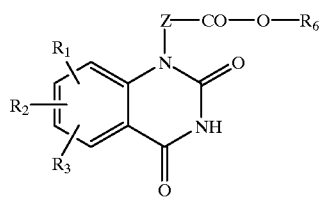

(III)

wherein

Z represents a methylene group or a methylene group which is substituted by an alkyl group;

$R_6$ represents an alkyl group or an aralkyl group;

$R_1$ and $R_2$ independently represent a hydrogen atom, a halogen atom, a nitro group, an azido group, an alkyl group, an alkyl group substituted by one or more halogen atoms, an alkenyl group, an alkenyl group substituted by one or more halogen atoms, an aralkyl group, an aralkyl group substituted by one or more halogen atoms, an alkoxy group, an alkoxy group substituted by one or more halogen atoms, an alkoxycarbonyl group, an alkoxycarbonyl group substituted by one or more halogen atoms, an acyloxy group, or an amino group represented by $XNR_4R_5$ in which X represents a direct bond, an alkylene group or a carbonyl group, and N, $R_4$ and $R_5$ may form together a five- or six-membered heterocyclic ring which optionally contains another nitrogen atom, in addition to the N atom attached to X, which is substituted with an alkyl group, an aralkyl group, or a phenylcarbonyl group or when X is a direct bond or an alkylene group, $R_4$ and $R_5$ independently may additionally represent an alkyl group or when X is a carbonyl group, $R_4$ and $R_5$ independently may additionally represent an acyloxy alkyl group;

$R_3$ represents a hydrogen atom, a halogen atom, a nitro group, an azido group, an alkyl group, an alkyl group substituted by one or more halogen atoms, an alkenyl group, an alkenyl group substituted by one or more halogen atoms, an aralkyl group, an aralkyl group substituted by one or more halogen atoms, an alkoxy group, an alkoxy group substituted by one or more halogen atoms, an alkoxycarbonyl group, or an alkoxycarbonyl group substituted by one or more halogen atoms, which comprises reacting a tetrahydroquinazoline represented by the formula (I):

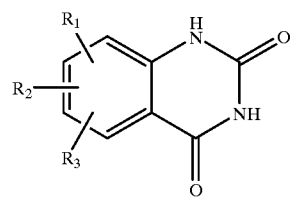

(I)

wherein $R_1$, $R_2$ and $R_3$ are as defined above, with hexamethyldisilazane; and reacting the resultant product with a chloroalkanoate represented by the formula (II):

Cl—Z—CO—O—$R_6$ (II)

wherein Z and $R_6$ are as defined above in the presence of an iodide of an alkali metal, followed by desilylation.

4. The process according to claim 1, wherein $R_6$ of the chloroalkanoate (II) is a lower alkyl group.

5. The process according to claim 2, wherein Z of the chloroalkanoate (II) is methylene or methylmethylene.

6. The process according to claim 1, wherein the chloroalkanoate (II) is ethyl chloroacetate.

7. The process according to claim 1, wherein the chloroalkanoate (II) is used in a 1- to 5-fold molar amount relative to the tetrahydroquinazolines (I).

8. The process according to claim 1, wherein the iodide of the alkaline metal is potassium iodide or sodium iodide.

9. The process according to claim 1, which is carried out in at least one solvent selected from an aromatic hydrocarbon, a hydrocarbon halide and an ether solvent.

10. The process according to claim 9, wherein the solvent is an aromatic hydrocarbon substituted with halogen.

11. The process according to claims 1, wherein the reaction between tetrahydroquinazolines (I) with hexamethyldisilazane is carried out under a reduced pressure and/or in an inert gas flow.

12. The process according to claim 1, wherein the reaction with a chloroalkanoate (II) is carried out while distilling off the generated the contents which have a lower boiling point.

13. The process as claimed in claim 2, wherein Z represents a methylene group which is substituted by an alkyl group.

14. The process as claimed in claim 2, wherein said alkyl group, said alkenyl group, said aralkyl group, said alkoxy group and said alkoxycarbonyl group represented by $R_1$ are substituted with one or more halogen atoms.

15. The process as claimed in claim 2, wherein said alkyl group, said alkenyl group, said aralkyl group, said alkoxy group and said alkoxycarbonyl group represented by $R_2$ are substituted with one or more halogen atoms.

16. The process as claimed in claim 2, wherein said alkyl group, said alkenyl group, said aralkyl group, said alkoxy group and said alkoxycarbonyl group represented by $R_3$ are substituted with one or more halogen atoms.

17. The process as claimed in claim 1, wherein said another hetero atom in addition to the N atom is a second nitrogen atom.

* * * * *